(12) United States Patent
Giberson et al.

(10) Patent No.: US 7,673,545 B1
(45) Date of Patent: Mar. 9, 2010

(54) TISSUE SLICING DEVICE

(76) Inventors: Richard T. Giberson, 1059 Filbert Ave., Chico, CA (US) 95926; Robert L. Honan, 2810 Highway 32, Chico, CA (US) 95973

( * ) Notice: Subject to any disclaimer, the term of this patent is extended or adjusted under 35 U.S.C. 154(b) by 1101 days.

(21) Appl. No.: 11/101,957

(22) Filed: Apr. 8, 2005

Related U.S. Application Data

(60) Provisional application No. 60/561,113, filed on Apr. 9, 2004, provisional application No. 60/635,118, filed on Dec. 11, 2004.

(51) Int. Cl.
*B26D 1/03* (2006.01)
*B26D 7/06* (2006.01)

(52) U.S. Cl. ............... 83/165; 83/166; 83/310; 83/409; 83/421; 83/425.3; 83/435.11; 83/446; 83/734; 83/881; 83/884

(58) Field of Classification Search .......... 83/409.2, 83/422, 425.3, 425.4, 446, 881, 915.5, 37, 83/435.11, 730, 882, 915.3, 162, 165, 166, 83/310, 409, 421, 425.2, 447, 508.2, 508.3, 83/734, 863–865, 873, 874, 876, 883–885, 83/932; 30/279.2, 279.4, 279.6, 283, 284, 30/287, 289, 293, 301, 304
See application file for complete search history.

(56) References Cited

U.S. PATENT DOCUMENTS

| | | | | |
|---|---|---|---|---|
| 547,433 A * | 10/1895 | Hazewinkel | ............... | 83/422 |
| 609,896 A * | 8/1898 | Morris | ................. | 83/444 |
| 739,044 A * | 9/1903 | Wilkin et al. | ............... | 83/811 |
| 888,297 A * | 5/1908 | Bell | ............... | 30/363 |
| 2,241,650 A * | 5/1941 | Spang | ............... | 83/873 |
| 2,445,488 A * | 7/1948 | Luteran | ............... | 83/35 |
| 2,941,560 A * | 6/1960 | McCaffery | ............... | 83/882 |
| 3,347,289 A * | 10/1967 | Kotesovic et al. | ............... | 83/876 |
| 4,041,822 A * | 8/1977 | Gabel | ............... | 83/409.2 |
| 4,276,798 A * | 7/1981 | Gottschalk | ............... | 83/430 |
| 5,036,590 A * | 8/1991 | Reinke et al. | ............... | 30/304 |
| 5,148,729 A | 9/1992 | Krumdieck | ............... | 83/411.1 |
| 5,522,294 A | 6/1996 | Krumdieck | ............... | 83/411.1 |
| 5,678,465 A | 10/1997 | Krumdieck | ............... | 83/36 |
| 5,860,348 A * | 1/1999 | Morse et al. | ............... | 83/864 |
| 6,041,686 A | 3/2000 | Lihl et al. | ............... | 83/628 |
| 6,458,598 B1 | 10/2002 | Huang | ............... | 436/176 |
| 6,736,041 B2 * | 5/2004 | Portnoy | ............... | 83/404.1 |
| 6,966,246 B2 * | 11/2005 | Yeh | ............... | 83/76.7 |

* cited by examiner

*Primary Examiner*—Clark F. Dexter
(74) *Attorney, Agent, or Firm*—William Bodnar

(57) ABSTRACT

A tissue slicing device is comprised of parallel circular blades coaxially connected to a rotary shaft. The blades are separated by gaps. A guide member is supported by a hinge adjacent the blades. An adjustment screw is positioned behind the guide member to control the distance between the guide member and the blades. The device includes a tissue carrier which is comprised of a base member and parallel plates extending from a top side of the base member. The plates are spaced to correspond with the gaps between the blades. Holes in the plates are aligned to define a tissue chamber for receiving a tissue sample. When the tissue carrier is positioned on the guide member and the blades rotated to drive the tissue carrier along the guide member, the tissue chamber is driven into the blades so the tissue sample is simultaneously cut into a plurality of slices.

16 Claims, 5 Drawing Sheets

TISSUE SLICING DEVICE

CROSS REFERENCE TO RELATED APPLICATIONS

We claim the priority of provisional patent applications 60/561,113 filed on 9 Apr. 2004, and 60/635,118 filed on 11 Dec. 2004.

BACKGROUND OF THE INVENTION

1. Field of the Invention

The invention broadly relates to biological tissue cutting devices.

2. Prior Art

Biological tissues for surgical pathology must be cut for chemical processing and embedding in paraffin. The cut tissues must be less than the inside dimensions of a standardized processing cassette which receives the tissues. The most commonly used tool is a hand tool such as a scalpel, knife, or razor blade, but it results in pieces with inconsistent dimensions. The thickness of the tissues directly affect the fixation rate in a fixative, the first step in the chemical processing. The quality of the fixation directly affects many of the downstream diagnostic tests. Therefore, tissue pieces with different thicknesses have different qualities of fixation that affect diagnostic testing.

There are tissue slicing instruments for making extremely thin slices measured in micrometers or even nanometers. These instruments cut only one slice at a time. The extreme thinness of their cuts require hardening the tissue by freezing or fixation in a rigid medium, such as paraffin. They are not suitable for cutting thicker slices, or cutting soft tissue.

BRIEF SUMMARY OF THE INVENTION

An object of the present tissue slicing device is to slice a tissue sample into multiple pieces of uniform thickness in a single cutting motion.

Another object is to be adjustable in cutting thickness.

Another object is to reliably eject the cut tissue from the slicing device.

The tissue slicing device is comprised of parallel circular blades coaxially connected to a rotary shaft. The blades are separated from each other by gaps. A guide member is supported by a hinge adjacent the blades. An adjustment screw is positioned behind the guide member. The distance between the guide member and the blades is adjustable by turning the screw. The slicing device includes a tissue carrier which is comprised of a base member and parallel plates extending from a top side of the base member. The plates are spaced from each other to correspond with the gaps between the blades. Holes in the plates are aligned with each other to define a tissue chamber for receiving a tissue sample. When the tissue carrier is positioned on the guide member and the blades are rotated to drive the tissue carrier along the guide member, the tissue chamber is driven into interference with the blades so that the tissue sample is simultaneously cut into a plurality of slices.

Figure 1:
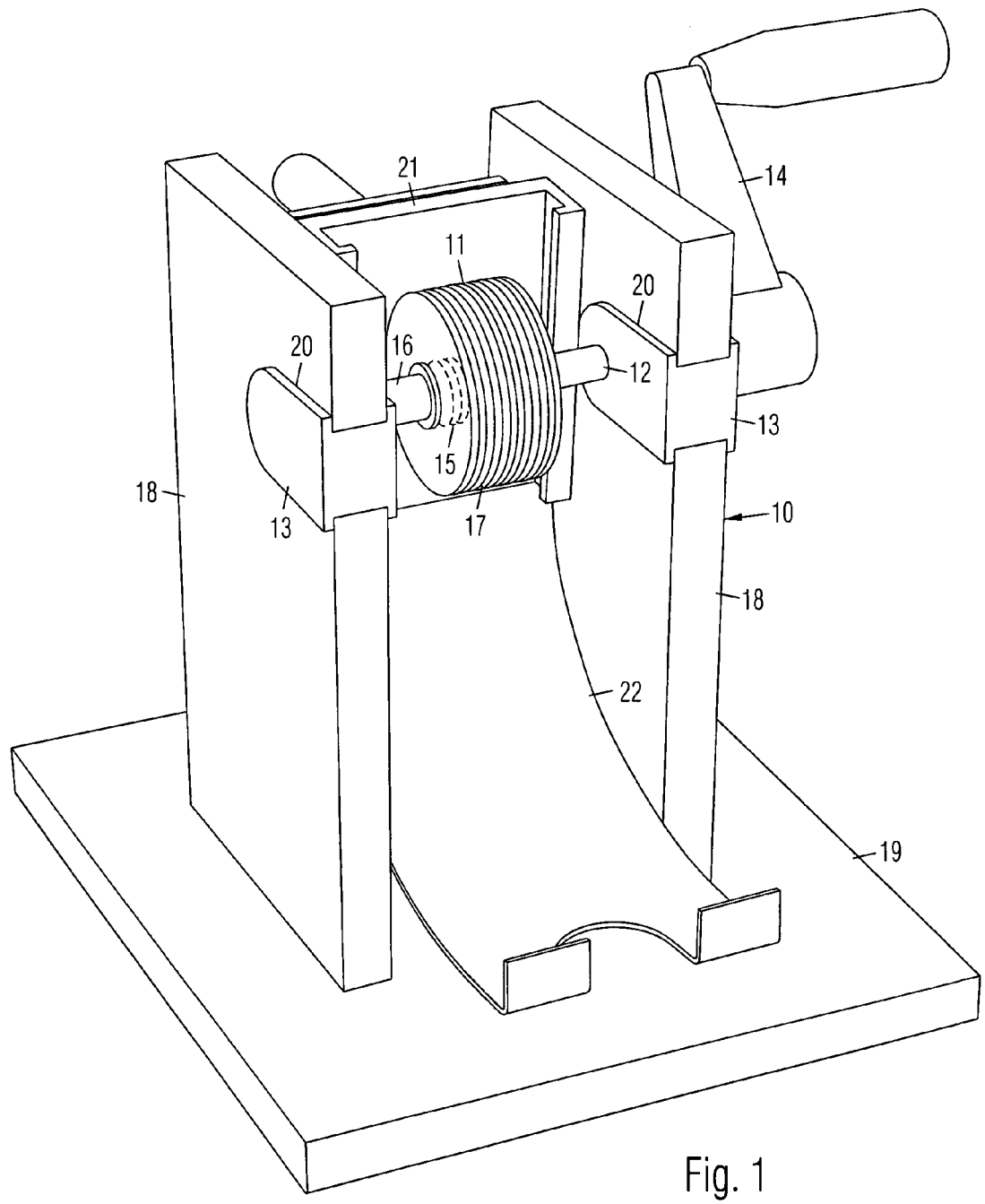
FIG. 1 is a front perspective view of the tissue slicing device.

| DRAWING REFERENCE NUMERALS | |
|---|---|
| 10. Tissue Slicing Device | 11. Circular Blade |
| 12. Rotary Shaft | 13. Bearing |
| 14. Hand Crank | 15. Spacer |
| 16. Fastener | 17. Gap |
| 18. Wall | 19. Base |
| 20. Bearing Slot | 21. Guide Member |
| 22. Output Tray | 23. Hinge |
| 24. Adjustment Screw | 25. Mounting Member |
| 26. Spring | 27. Tissue Carrier |
| 28. Base Member | 29. Plate |
| 30. Slot | 31. Hole |
| 32. Tissue Chamber | 33. Break |
| 34. Living Hinge | 35. Tissue Sample |
| 36. Alignment Card | 37. Adhesive |

DETAILED DESCRIPTION OF THE INVENTION

FIG. 1

A preferred embodiment of a tissue slicing device 10 is shown in a front perspective view in FIG. 1. It is comprised of a plurality of parallel circular blades 11 coaxially connected to a rotary shaft 12 supported on bearings 13. A hand crank 14 is attached to shaft 12 for manually turning blades 11, although a motor (not shown) may be attached instead. Blades 11 are axially separated from each other by respective spacers 15 and secured on shaft 12 by a fastener 16. The width of gaps 17 between blades 11 are adjustable by removing fastener 16, removing blades 11 and spacers 15 from shaft 12, and reassembling blades 11 on shaft 12 with spacers of a different thickness.

Shaft 12 is positioned between a pair of supporting walls 18 attached on a base 19. Bearings 13 are detachably received in bearing slots 20 in respective walls 18. A shield (not shown) may be provided between walls for covering blade. A guide member 21 is positioned behind blades 11. An output tray 22 is positioned below guide member 21 in alignment therewith.

FIGS. 2-3

Figure 2:
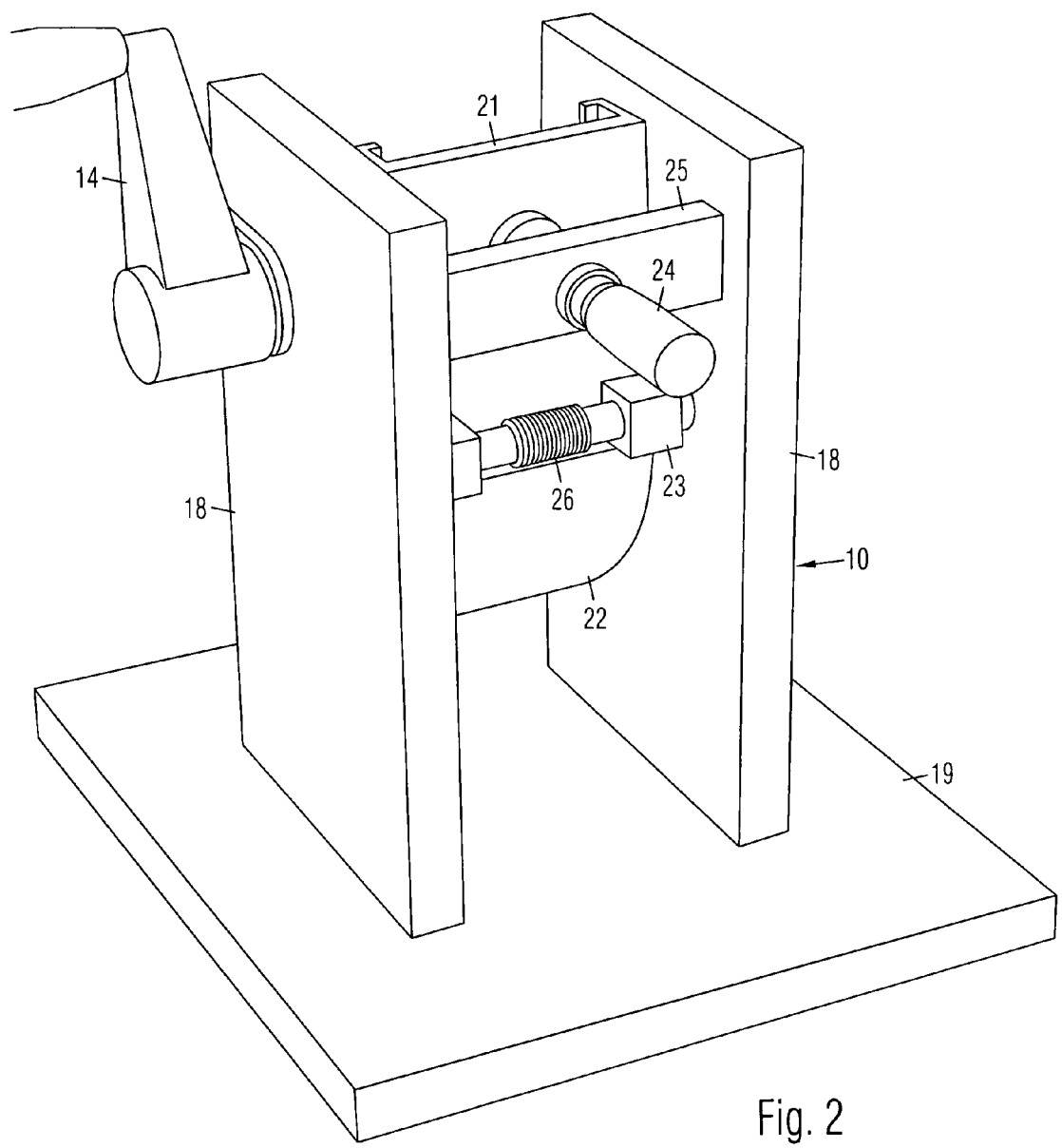
FIG. 2 is a rear perspective view thereof.
Figure 3:
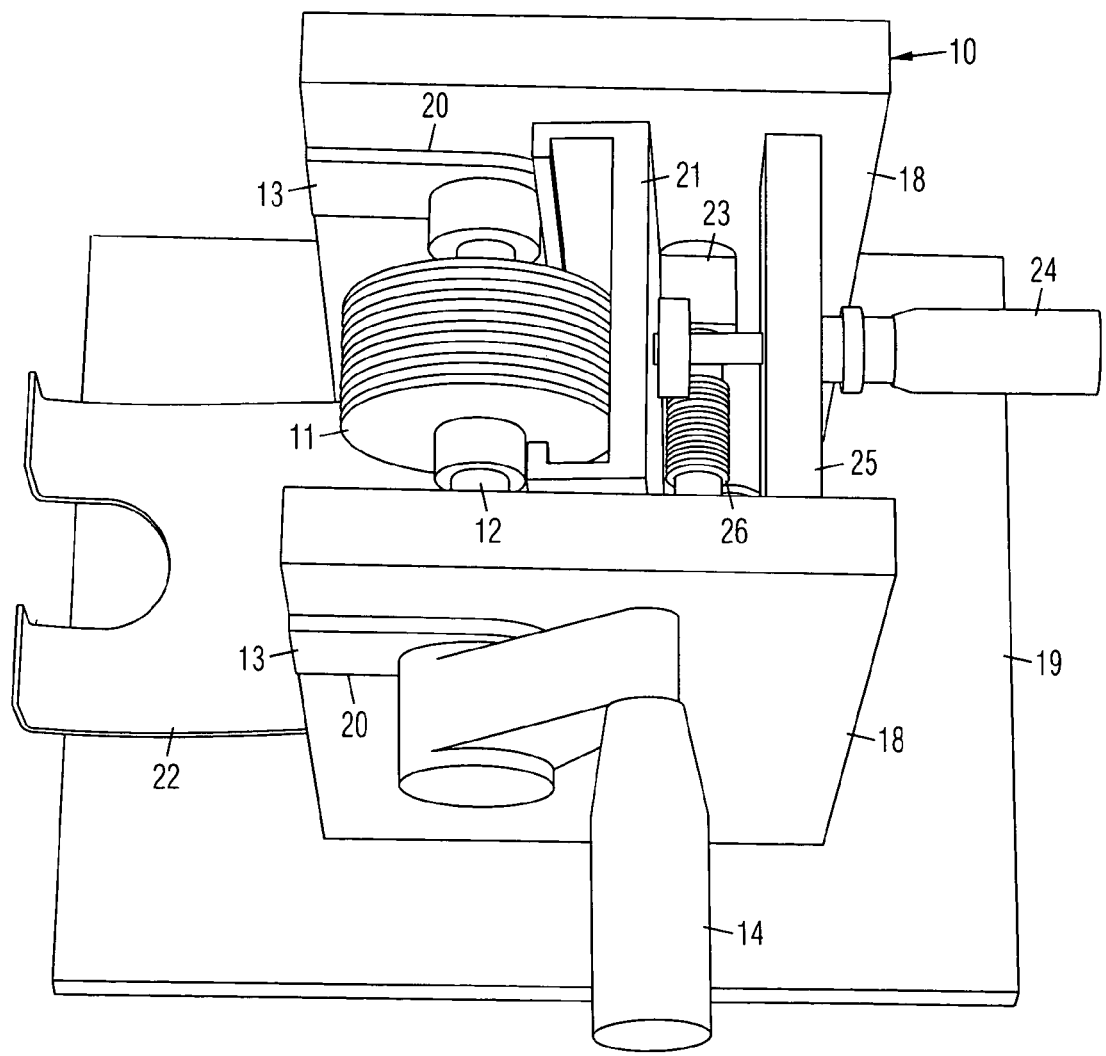
FIG. 3 is a top perspective view thereof
Figure 4:
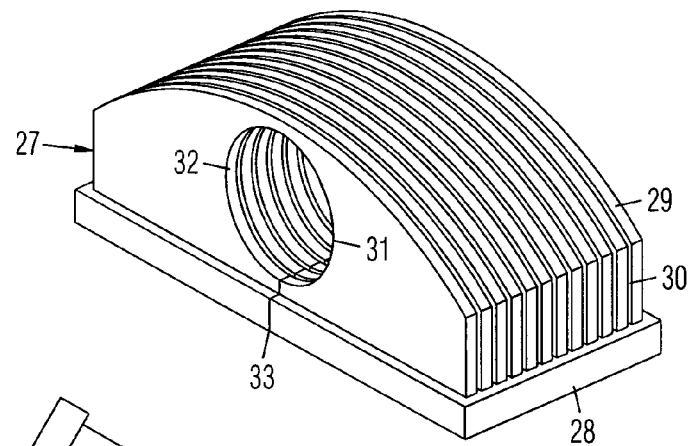
FIG. 4 is a top perspective view of a tissue carrier thereof

Slicing device 10 is shown in a rear perspective view in FIG. 2 and a top perspective view in FIG. 3. A hinge 23 extending between walls 18 is connected to a back side of guide member 21. An adjustment screw 24 is attached to a mounting member 25 connected between walls 18 behind guide member 21. The back of guide member 21 is biased against an inner end of adjustment screw 24 by a spring 26 on hinge 23. The distance between guide member 21 and blades 11 is adjustable by turning an outer end of screw 24.

FIGS. 4-6

Slicing device 10 is also comprised of a tissue carrier 27 which includes a base member 28 and parallel plates 29 extending from a top side of base member 28. Plates 29 are positioned to correspond with gaps 17 between blades 11 (FIG. 1), and are spaced from each other to define slots 30 there between. Plates 29 have a thickness which is less than the thickness of gaps 17 between blades 11. Plates 29 are provided with respective holes 31 which are aligned with each other to define a tissue chamber 32. A break 33 extends across the bottom of tissue chamber 32 and base member 28.

Figure 5:
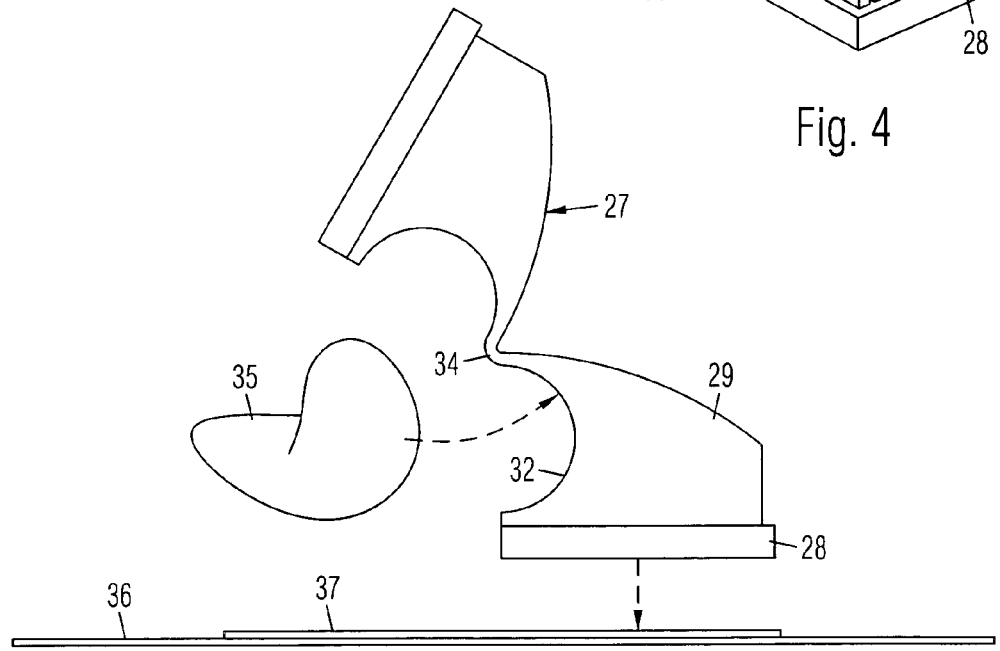
FIG. 5 is a side view of the tissue carrier opened for receiving a tissue sample.
Figure 6:
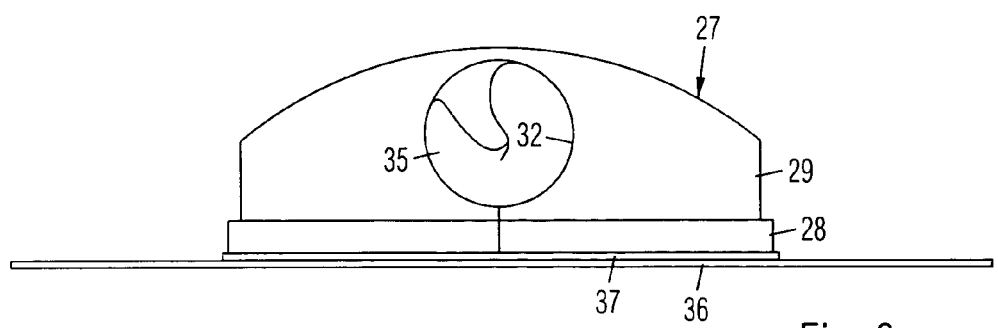
FIG. 6 is a side view of the tissue carrier closed around the tissue sample.

Tissue carrier 27 is comprised of a resilient material, such as silicon. Tissue chamber 32 is opened by pivoting apart base member 28 as shown in FIG. 5. An upper portion of tissue chamber 32 is thin enough to be a living hinge 34. A piece of tissue sample 35 is positioned inside chamber 32, and base member 28 is moved back together as shown in FIG. 6. Base member 28 is attached to an alignment card 36 with double sided tape 37. Alternatively, break 33 may be eliminated and tissue sample 35 is pushed into tissue chamber 32 through one of its open ends.

FIG. 7

Figure 7:
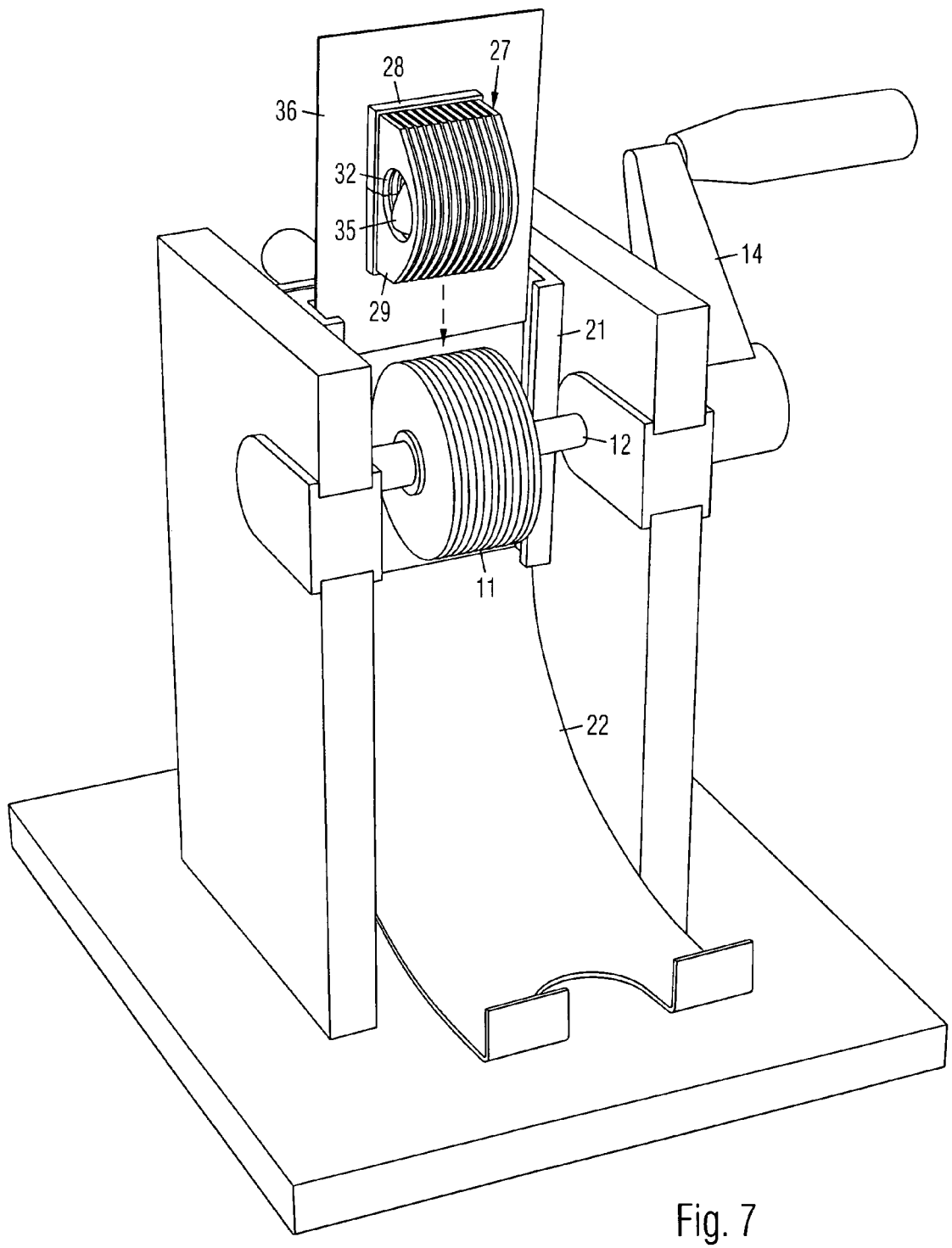
FIG. 7 is a top perspective view of the tissue carrier being fed through the tissue slicing device.

In FIG. 7, alignment card 36 is slipped onto guide member 21 above blades 11 until tissue carrier 27 contacts blades 11. Blades 11 are rotated by turning crank 14 to drive carrier 27 along guide member 21. When tissue chamber 32 is driven into interference with blades 11, tissue sample 35 is simultaneously cut into a plurality of uniformly thick slices. Tissue carrier 27 carries all the cut pieces and ensures that none is trapped between blades 11. After tissue carrier 27 is driven past blades 11, it is dropped onto output tray 22 below.

Although the foregoing description is specific, it should not be considered as a limitation on the scope of the invention, but only as an example of the preferred embodiment. Many variations are possible within the teachings of the invention. Therefore, the scope of the invention should be determined by the appended claims and their legal equivalents, not by the examples given.

We claim:

1. A tissue slicing device, comprising:
a rotary shaft;
a plurality of parallel circular blades coaxially connected to the rotary shaft and axially separated from each other by respective gaps;
a guide member positioned adjacent the blades and parallel to the shaft for receiving a tissue sample, the guide member extending past the blades such that the tissue sample is moved along the guide member during cutting; wherein
when the tissue sample is positioned on the guide member and the blades are rotated to drive the tissue sample along the guide member, the tissue sample is simultaneously cut by the blades into a plurality of slices, and
further including supporting walls supporting the shaft, a hinge having a pivot axis that extends substantially parallel to the rotary shaft, the hinge supporting the guide member relative to the walls for pivoting of the guide member about the pivot axis, an adjustment screw supported by a mounting member which is fixed relative to the walls, and a spring biasing the guide member against an inner end of the adjustment screw,
wherein a distance between the guide member and the blades is adjustable by turning the screw.

2. The tissue slicing device of claim 1, further including bearings supporting the shaft between the walls, wherein the bearings are received in respective bearing slots in the walls.

3. The tissue slicing device of claim 1, further including respective spacers between the blades.

4. The tissue slicing device of claim 1, further including an alignment card, and a tissue carrier comprising a base member, the tissue carrier guided on the guide member, wherein the base member of the tissue carrier is attached to the alignment card.

5. The tissue slicing device of claim 1, further including an output tray positioned below the guide member.

6. A tissue slicing device, comprising:
a rotary shaft;
a plurality of parallel circular blades coaxially connected to the rotary shaft and axially separated from each other by respective gaps;
a guide member positioned adjacent the blades parallel to the shaft;
a tissue carrier comprising a base member and a plurality of parallel plates extending from a side of the base member, wherein the plates are spaced from each other and positioned to correspond with the gaps between the blades, the plates are provided with respective holes which are aligned with each other to define a tissue chamber for receiving a tissue sample; wherein
when the tissue carrier is positioned on the guide member and the blades are rotated to drive the tissue carrier along the guide member, the tissue chamber is driven into interference with the blades for simultaneously cutting the tissue sample into a plurality of slices; and
further including supporting walls supporting the shaft, a hinge supporting the guide member relative to the walls, an adjustment screw supported by a mounting member which is fixed relative to the walls, and a spring biasing the guide member against an inner end of the adjustment screw, wherein a distance between the guide member and the blades is adjustable by turning the screw.

7. The tissue slicing device of claim 6, further including bearings supporting the shaft between the walls, wherein the bearings are received in respective bearing slots in the walls.

8. The tissue slicing device of claim 6, further including respective spacers between the blades.

9. The tissue slicing device of claim 6, further including an alignment card, wherein the base member of the tissue carrier is attached to the alignment card.

10. The tissue slicing device of claim 6, further including an output tray positioned below the guide member.

11. A tissue slicing device, comprising:
a plurality of supporting walls;
a rotary shaft supported by the supporting walls;
a plurality of parallel circular blades coaxially connected to the rotary shaft and axially separated from each other by respective gaps;
a guide member positioned adjacent the blades parallel to the shaft;
a hinge supporting the guide member relative to the supporting walls;
an adjustment screw supported by a mounting member which is fixed relative to the supporting walls;
a spring biasing the guide member against an inner end of the adjustment screw, wherein a distance between the guide member and the blades is adjustable by turning the screw; and
a tissue carrier, comprising:
a base member and a plurality of parallel plates extending from a side of the base member, wherein the plates are spaced from each other and positioned to correspond with the gaps between the blades;
respective holes in the plates which are aligned with each other to define a tissue chamber for receiving a tissue sample;
a break across the base member of the tissue carrier and a portion of the tissue chamber adjacent the base member, wherein the tissue carrier is comprised of a resilient material, so that the tissue chamber is opened by pivoting apart the base member using a portion of the tissue chamber opposite the break as a living hinge; wherein when the tissue carrier is positioned on the guide member and the blades are rotated to drive the tissue carrier along the guide member, the tissue chamber is driven into interference with the blades for simultaneously cutting the tissue sample into a plurality of slices.

12. The tissue slicing device of claim 11, further including respective spacers between the blades.

13. The tissue slicing device of claim 12, further including an alignment card, wherein the base member of the tissue carrier is attached to the alignment card.

14. The tissue slicing device of claim 12, further including an output tray positioned below the guide member.

15. The tissue slicing device of claim 11, further including an alignment card, wherein the base member of the tissue carrier is attached to the alignment card.

16. The tissue slicing device of claim 11, further including an output tray positioned below the guide member.

* * * * *